United States Patent [19]

Nakagawa et al.

[11] 4,294,835
[45] Oct. 13, 1981

[54] 2-HYDROXY BENZAMIDE DERIVATIVES AND USE THEREOF AS A FUNGICIDE

[75] Inventors: Taizo Nakagawa; Hiroshi Matsumoto, both of Ageo; Kaoru Ohmori, Okegawa; Shizuo Shimano; Kengo Koike, both of Ageo, all of Japan

[73] Assignee: Nippon Kayaku Kabushiki Kaisha, Tokyo, Japan

[21] Appl. No.: 123,766

[22] Filed: Feb. 20, 1980

[30] Foreign Application Priority Data

Feb. 27, 1979 [JP] Japan ................................ 54-21350

[51] Int. Cl.³ .................. C07C 103/26; C07D 213/75; A01N 43/40; A01N 37/24
[52] U.S. Cl. .................................... 424/263; 424/320; 546/291; 560/16; 564/177; 564/179
[58] Field of Search .................. 546/291; 260/559 T; 424/263, 320; 564/177, 179; 560/16

[56] References Cited
U.S. PATENT DOCUMENTS 4,200,632  4/1980  Nakagawa et al. ................ 564/177

OTHER PUBLICATIONS

Carter et al., Ann. Appl. Biol., vol. 75, pp. 49-55, printed in Great Britain (1973).
Burger, Medicinal Chemistry, Second Edition, pp. 75-77, Interscience Publishers, 1960.

Primary Examiner—Alan L. Rotman
Attorney, Agent, or Firm—Russell & Nields

[57] ABSTRACT

A compound represented by the formula:

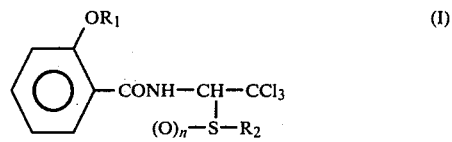

wherein $R_1$ is hydrogen, acetyl or alkoxycarbonyl having 1-3 carbon atoms of the alkoxy, $R_2$ is alkyl having 1-12 carbon atoms, alkoxycarbonylmethyl having 1-12 carbon atoms of the alkoxy, benzyl, 2-pyridyl, cyclohexyl phenyl or phenyl substituted by one or two members selected from the group consisting of alkyl having 1-3 carbon atoms, halogen and nitro, and n is 0 or 1, with the proviso that when n is one, $R_1$ represents acetyl exclusively, and use thereof as a fungicide.

7 Claims, No Drawings

2-HYDROXY BENZAMIDE DERIVATIVES AND USE THEREOF AS A FUNGICIDE

DETAILED DESCRIPTION OF THE INVENTION

The present invention relates to 2-hydroxybenzamide derivatives represented by the formula:

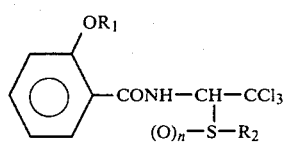

wherein $R_1$ is hydrogen, acetyl or alkoxycarbonyl having 1-3 carbon atoms of the alkoxy, $R_2$ is alkyl having 1-12 carbon atoms, alkoxycarbonylmethyl having 1-12 carbon atoms of the alkoxy, benzyl, 2-pyridyl, cyclohexyl, phenyl or phenyl substituted by one or two members selected from the group consisting of alkyl having 1-3 carbon atoms, halogen and nitro, and n is 0 or 1, with the proviso that when n is 1, R, represents acetyl exclusively; a fungicidal composition for agriculture and horticulture comprising one or more of said 2-hydroxybenzamide derivatives as effective components and a method of preventing fungi.

As fungicides used for protecting agricultural and horticultural plants from diseases, there have been used organomercurous compounds, organic chlorine compounds, organic phosphorous compounds and gaseous compounds. However, the organomercurous compounds have a very strong toxicity to humans and beasts. The organic chlorine compounds have a considerable phytotoxicity for plants. Since they are required in large amounts and in a high concentration for obtaining a satisfactory prevention effect, they are liable to remain in the plant body or in the soil. The gaseous fungicides have defects of irritative smell or bad smell.

After investigations for the development of agricultural and horticultural fungicides free of said defects, the inventors have found that compounds represented by formula (I) are highly effective in preventing agricultural and horticultural plants from diseases, particularly a remarkable effect against the clubroot of Cruciferous plants and rice blast disease with only a low concentration. The present invention has been attained on the basis of this finding.

Of benzamide compounds relating to the present invention, there are disclosed in Ann. Appl. Biol. (1973), Vol. 75, pp. 49-55 N-(1-methylthio-2,2,2-trichloroethyl)-benzamide, N-(1-methylthio-2,2,2-trichloroethyl)-2-chlorobenzamide and N-(1-methylthio-2,2,2-trichloroethyl)-2-methylbenzamide, but none of them has fungicidal effect. Those compounds of the present invention are new ones having strong fungicidal effect.

The compounds of the present invention have only a very low toxicity to humans and beasts, do not damage plants, are free of irritative or unpleasant smell, and are capable of preventing diseases of plants in a low concentration. Therefore, the compounds can be used as ideal agricultural and horticultural fungicides in only a small amount without fear of soil contamination.

As examples of alkoxycarbonyls having 1-3 carbon atoms of the alkoxy of formula (I) there may be mentioned methoxycarbonyl, ethoxycarbonyl and propoxycarbonyl.

As alkyls having 1-12 carbon atoms there are methyl, ethyl, propyl, butyl, octyl, nonyl, decyl and dodecyl.

Furthermore as examples of alkoxycarbonylmethyls having 1-12 carbon atoms of the alkoxy, there can be mentioned methoxycarbonylmethyl, ethoxycarbonylmethyl, propoxycarbonylmethyl, butoxycarbonylmethyl, octyloxycarbonylmethyl, decyloxycarbonylmethyl and dodecyloxycarbonylmethyl. As halogens there are chloro and bromo.

The preferred compounds of the present invention are the following compounds of formula (I) wherein $R_1$ is hydrogen or acetyl, $R_2$ is alkyl having 1-14 carbon atoms and n is O.

The compounds of the present invention are prepared as follows:

A compound represented by the formula:

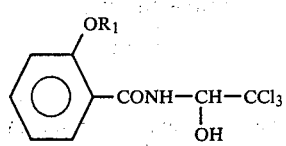

wherein $R_1$ has the same meaning as above, is reacted with a halogenating agent such as thionyl chloride to prepare a compound represented by the formula:

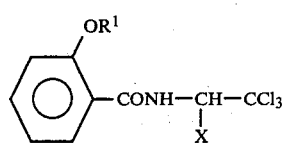

wherein $R_1$ has the same meaning as above and X represents halogen. The reaction is usually conducted in a solvent such as methyl chloroform, dichloromethane or carbon tetrachloride in the presence of a halogenating catalyst such as dimethylformamide.

Then the compound of formula (III) is reacted with a compound represented by the formula:

$R_2SH$     (IV)

wherein $R_2$ has the same meaning as above, preferably in an inert solvent such as dichloromethane or acetone in the presence of a base, and a compound of formula (I) wherein n is O:

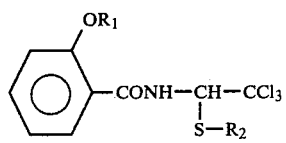

(wherein $R_1$ has the same meaning as above) can be obtained.

As examples of compounds of formula (IV) there may be mentioned alkyl mercaptans such as methyl mercaptan, ethyl mercaptan, propyl mercaptan, butyl mercaptan, octyl mercaptan, nonyl mercaptan, decyl mercaptan and dodecyl mercaptan, alkoxycarbonylmethyl mercaptans such as methylcarbonylmethyl mercaptan, ethylcarbonylmethyl mercaptan, propylcarbonylmethyl mercaptan, octylcarbonylmethyl mercaptan and dodecylcarbonylmethyl mercaptan, benzyl mercaptan, 2-pyridyl mercaptan, cyclohexyl mercaptan, phenyl mercaptan, and phenyl mercaptans substituted by one or two members selected from the group consisting of methyl, propyl, butyl, chloro and nitro.

As a base, there are used hydroxides of alkaline metals (for example, sodium hydroxide and potassium hydrochloride) or tertiary amines (for example, triethyl amine and pyridine).

When a compound of formula (V) wherein $R_1$ represents acetyl is hydrolyzed in the presence of an acid catalyst (for example, hydrochloric acid, sulfuric acid and hydrogen chloride) usually in a solvent such as ethanol, a compound of formula (I) wherein $R_1$ is hydrogen and n is O:

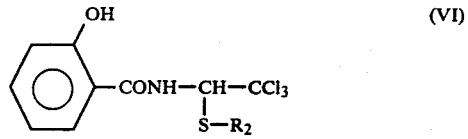
(VI)

can be obtained.

Moreover, when a compound of formula (V) wherein $R_1$ represents acetyl is oxidized usually with an oxidizing agent such as hydrogen peroxide in a solvent such as acetic acid as a rule, a compound of formula (I) wherein $R_1$ is acetyl and n is 1:

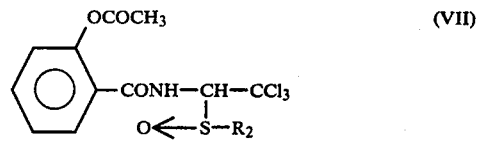
(VII)

can be obtained.

In addition, when a compound of formula (VI) is reacted with a compound represented by the formula:

(VIII)

(wherein $R_4$ is lower alkyl) such as methyl chlorocarbonate or ethyl chlorocarbonate usually in a solvent such as acetone in the presence of a base (same as defined above), a compound of formula (I) wherein $R_1$ is alkoxycarbonyl and n is 0:

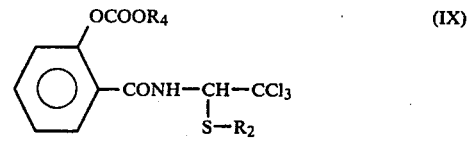
(IX)

(wherein $R_2$ and $R_4$ are as defined above respectively) can be obtained.

The compound of formula (II) used as a starting material can be prepared by reacting o-acetylsalicylamide with chloral usually in a solvent such as methyl chloroform.

The typical compounds of the present invention prepared by the procedures mentioned above are shown in Table 1.

TABLE 1

| Compound No. | $R_1$ | $R_2$ | n | Physical properties (m.p. or refractive index) |
|---|---|---|---|---|
| 1 | —COCH$_3$ | —C$_2$H$_5$ | 0 | 100 ~ 102° C. |
| 2 | —COCH$_3$ | —C$_3$H$_7$(n) | 0 | 72 ~ 73° C. |
| 3 | —COCH$_3$ | —C$_3$H$_7$(iso) | 0 | 73 ~ 74° C. |
| 4 | —COCH$_3$ | —C$_4$H$_9$(n) | 0 | 54 ~ 56° C. |
| 5 | —COCH$_3$ | —C$_4$H$_9$(iso) | 0 | 74 ~ 75° C. |
| 6 | —COCH$_3$ | —C$_4$H$_9$(sec) | 0 | 80 ~ 82° C. |
| 7 | —COCH$_3$ | —C$_4$H$_9$(t) | 0 | 126 ~ 128° C. |
| 8 | —COCH$_3$ | —C$_8$H$_{17}$(n) | 0 | 67 ~ 68° C. |
| 9 | H | —CH$_2$—⟨phenyl⟩ | 0 | 76 ~ 77° C. |
| 10 | H | ⟨pyridyl⟩ | 0 | 128 ~ 130° C. |
| 11 | H | —CH$_2$COOCH$_3$ | 0 | 84 ~ 86° C. |
| 12 | H | —CH$_2$COOC$_2$H$_5$ | 0 | $n_D^{25}$ 1.5749 |
| 13 | H | —CH$_2$COOC$_3$H$_7$(iso) | 0 | $n_D^{25}$ 1.5648 |
| 14 | H | —CH$_2$COOC$_8$H$_{17}$(n) | 0 | $n_D^{25}$ 1.5031 |
| 15 | H | —CH$_3$ | 0 | 98 ~ 99° C. |
| 16 | H | —C$_2$H$_5$ | 0 | 117 ~ 119° C. |
| 17 | H | —C$_3$H$_7$(n) | 0 | 120 ~ 112° C. |
| 18 | H | —C$_3$H$_7$(iso) | 0 | 131 ~ 133° C. |
| 19 | H | —C$_4$H$_9$(n) | 0 | 62 ~ 64° C. |
| 20 | H | —C$_4$H$_9$(iso) | 0 | 108 ~ 110° C. |
| 21 | H | —C$_4$H$_9$(sec) | 0 | 106 ~ 108° C. |

TABLE 1-continued $$\underset{(O)_n \leftarrow S-R_2}{\underset{|}{\text{Ar-CONH-CH-CCl}_3}} \quad \text{(where Ar = 2-OR}_1\text{-phenyl)} \quad (I)$$

| Compound No. | R₁ | R₂ | n | Physical properties (m.p. or refractive index) |
|---|---|---|---|---|
| 22 | H | —C₄H₉(t) | 0 | 154 ~ 156° C. |
| 23 | H | —C₆H₁₁(cyclohexyl) | 0 | 149 ~ 152° C. |
| 24 | H | —C₈H₁₇(n) | 0 | $n_D^{25}$ 1.5510 |
| 25 | H | —C₆H₅ (phenyl) | 0 | 103 ~ 106° C. |
| 26 | H | —C₆H₄—CH₃ | 0 | 161 ~ 163° C. |
| 27 | H | —C₆H₄—C₃H₇(iso) | 0 | 145 ~ 146° C. |
| 28 | H | —C₆H₄—C₄H₉(t) | 0 | 139 ~ 140° C. |
| 29 | H | —C₆H₄—Cl | 0 | 138 ~ 140° C. |
| 30 | H | —C₆H₄—NO₂ | 0 | 173 ~ 175° C. |
| 31 | H | —C₆H₃(Cl)(Cl) (dichlorophenyl) | 0 | 179 ~ 181° C. |
| 32 | —COOCH₃ | —C₃H₇(iso) | 1 | 90 ~ 92° C. |
| 33 | —COOCH₃ | —C₃H₇(iso) | 0 | 84 ~ 85° C. |
| 34 | —COOC₂H₅ | —C₄H₉(n) | 0 | $n_D^{25}$ 1.5350 |
| 35 | —COCH₃ | —CH₃ | 0 | 146 ~ 148° C. |
| 36 | H | —C₆H₁₃(n) | 0 | $n_D^{25}$ 1.5594 |
| 37 | H | —C₁₀H₂₁(n) | 0 | $n_D^{25}$ 1.5429 |
| 38 | H | —C₁₂H₂₅(n) | 0 | $n_D^{25}$ 1.5388 |
| 39 | —COCH₃ | —C₁₀H₂₁(n) | 0 | 48 ~ 49° C. |
| 40 | —COCH₃ | —C₁₂H₂₅(n) | 0 | 50 ~ 51° C. |
| 41 | —COCH₃ | —CH₂COOC₂H₅ | 0 | $n_D^{25}$ 1.5459 |
| 42 | —COCH₃ | —C₆H₅ | 0 | 111 ~ 113° C. |
| 43 | —COOCH₃ | —CH₂COOC₂H₅ | 0 | 58 ~ 60° C. |
| 44 | —COOC₂H₅ | —C₆H₅ | 0 | 77 ~ 79° C. |
| 45 | —COOC₄H₉(n) | —C₆H₁₃(n) | 0 | 64 ~ 65° C. |
| 46 | —COOC₄H₉(n) | —C₁₀H₂₁(n) | 0 | $n_D^{25}$ 1.5145 |
| 47 | —COOC₄H₉(n) | —C₁₂H₂₅(n) | 0 | $n_D^{25}$ 1.5113 |

For further illustration of methods of preparing the compounds of the present invention, the following examples are given.

EXAMPLE 1

N-(1-ethylthio-2,2,2-trichloroethyl)-2-acetoxybenzamide (Compound No. 1):

50 ml of dichloromethane was added to 7.9 g of N-(1,2,2,2-tetrachloroethyl)-2-acetoxybenzamide. 1.3 g of ethyl mercaptan was add to the solution under stirring and then 2.0 g of triethylamine was added dropwise thereto at 10°–15° C. After effecting the reaction at room temperature for one hour, water was added thereto and the solution was allowed to stand. Then the dichloromethane layer was separated out, dried with unhydrous sodium sulfate and concentrated to obtain 7.0 g of N-(1-ethylthio-2,2,2-trichloroethyl)-2-acetoxybenzamide as white crystals.

Melting point: 100°–102° C.

EXAMPLE 2

N-(1-n-octyloxycarbonylmethylthio-2,2,2-trichloroethyl)-2-hydroxybenzamide (Compound No. 14)

5 g of thionyl chloride was added dropwise to the mixture of 10 g of N-(1-hydroxy-2,2,2-trichloroethyl)-2-hydroxybenzamide, 50 ml of carbon tetrachloride and 0.1 g of N,N-dimethylformamide under stirring. After effecting the reaction under reflux for one hour, the solvent was distilled off under reduced pressure to obtain N-(1,2,2,2-tetrachloroethyl)-2-hydroxybenzamide (m.p.: 113°–113.5° C.). Without taking out the compound thus resulted, thereto were added 50 ml of acetone and also 7.2 g of octyl thioglycolate (n), and the mixture was stirred at room temperature for one hour. The solvent was distilled off and the rest was purified by silica gel column chromatography to obtain 3.0 g of N-(1-n-octyloxycarbonylmethylthio-2,2,2-trichloroethyl)-2-hydroxybenzamide as a light yellow oily substance. $n_D^{25}$1.5031

EXAMPLE 3

N-(1-iso-propylthio-2,2,2-trichloroethyl)-2-hydroxybenzamide (Compound No. 18)

3.2 g of N-(1-iso-propylthio-2,2,2-trichloroethyl)-2-acetoxybenzamide, 30 ml of ethanol and 0.5 ml of 35% hydrochloric acid were mixed together and the reaction was effected while stirring under reflux for two hours. The solvent was distilled off, and the contents were washed with water and dried to obtain 2.7 g of N-(1-iso-propylthio-2,2,2-trichloroethyl)-2-hydroxybenzamide as white crystals.

Melting point: 131°–133° C.

EXAMPLE 4

N-(1-penylthio-2,2,2-trichloroethyl)-2-hydroxybenzamide (Compound No. 25)

10.3 g of a 20% acqueous NaOH solution was added dropwise to the mixture of 16.6 g of N-(1,2,2,2-tetrachloroethyl)-2-acetoxybenzamide, 70 ml of acetone and 5.3 g of phenyl mercaptan under stirring at 10°–15° C. The reaction was effected at room temperature for one hour. Water was added thereto, the dichloromethane layer was separated, and the solution was dried and concentrated. 100 ml of ethanol and 1.5 ml of 35% hydrochloric acid were added to the residue and the reaction was effected under reflux for two hours. The solvent was distilled off to obtain 14.5 g of N-(1-phenylthio-2,2,2-trichloroethyl)-2-hydroxybenzamide as white crystals.

Melting point: 103°–106° C.

EXAMPLE 5

N-(1-iso-propylsulfinyl-2,2,2-trichloroethyl)-2-acetoxybenzamide (Compound No. 32)

To 15.0 g of N-(1-iso-propylthio-2,2,2-trichloroethyl)-2-acetoxybenzamide was added 80 ml of acetic acid and 3.8 g of 35% hydrogen peroxide solution was added dropwise thereto under stirring. Then the reaction was effected at 40°–50° C. for three hours and the reaction mixture was poured into water. 100 ml of ethyl acetate was added thereto and the solution was separated, dried, concentrated, washed and dried again to obtain 12.3 g of N-(1-iso-propylsulfinyl-2,2,2-trichloroethyl)-2-acetoxybenzamide.

Melting point: 90°–92° C.

EXAMPLE 6

N-(1-n-butylthio-2,2,2-trichloroethyl)-2-ethoxycarbonyloxybenzamide (Compound No. 34)

13 g of ethyl chlorocarbonate was added to the mixture of 3.4 g of N-(1-n-butylthio-2,2,2-trichloroethyl)-2-hydroxybenzamide and 50 ml of acetone under stirring, and 1.0 g of triethylamine was added dropwise thereto at 0°–5° C. After effecting the reaction at room temperature for one hour, the solvent was distilled off under reduced pressure, 50 ml of water was added thereto and the solution was extracted with ethyl acetate. After washing the extract with water and drying, the solvent was distilled off to obtain 3.2 g of N-(1-n-butylthio-2,2,2-trichloroethyl)-2-ethoxycarbonyloxybenzamide as a brown oily substance. $n_D^{25}$1.5350

EXAMPLE 7

N-(1-iso-propylthio-2,2,2-trichloroethyl)-2-hydroxybenzamide (Compound No. 18)

14.2 g of N-(1-hydroxy-2,2,2-trichloroethyl)-2-hydroxybenzamide was mixed with 100 ml of dichloromethane, 7.2 g of thionyl chloride and 0.1 g of N,N-dimethylformamide and the reaction was effected while stirring under reflux for three hours. The solvent was distilled off to obtain N-(1,2,2,2-tetrachloroethyl)-2-hydroxybenzamide (m.p.: 113°–113.5° C.). Without taking this out, 100 ml of dichloromethane and 3.8 g of iso-propyl mercaptan were added thereto and then 4.0 g of pyridine was also added dropwise. After effecting the reaction at room temperature for one hour, water was added thereto, the dichloromethane layer was separated out, dried and concentrated to obtain 16.2 g of N-(1-iso-propylthio-2,2,2-trichloroethyl)-2-hydroxybenzamide as white crystals.

Melting point: 131°–133° C.

REFERENCE EXAMPLE 1

Preparation of N-(1,2,2,2-tetrachloroethyl)-2-acetoxybenzamide 17.9 g of o-acetylsalicylamide was suspended in 70 ml of methyl chloroform, 17.6 g of chloral was added thereto and the reaction was effected under stirring at 70°–75° C. for 3–4 hours. 28.2 g of N-(1-hydroxy-2,2,2-trichloroethyl)-2-acetoxybenzamide was obtained as white crystals. Melting point: 124°–126° C. This compound, 100 ml of methyl chloroform and 0.3 ml of N,N-dimethylformamide were mixed together and 13.4 g of thionyl chloride was added dropwise thereto under stirring. The mixture was heated at 60°–70° C. for three hours and the solvent was distilled off under reduced pressure to obtain 30.0 g of N-(1,2,2,2-tetrachloroethyl)-2-acetoxybenzamide as light yellow crystals. Melting point: 88°–90° C.

REFERENCE EXAMPLE 2

Preparation of N-(1,2,2,2-tetrachloroethyl)-2-hydroxybenzamide

To 14.2 g of N-(1-hydroxy-2,2,2-trichloroethyl)-2-hydroxybenzamide were added 100 ml of dichloromethane, 0.1 g of N,N-dimethylformamide and 7.2 g of thionyl chloride, and the reaction was effected while stirring under reflux for three hours. Excess thionyl chloride was distilled off together with the solvent under reduced pressure to obtain 15.1 g of N-(1,2,2,2-tetrachloroethyl)-2-hydroxybenzamide.

Melting point: 113°–113.5° C.

The compounds of the present invention are used as agricultural or horticultural fungicides sometimes solely but usually in various types of formulations, with carriers or other adjuvants, such as emulsion, wettable powder, dusts, granules and micro granules in compliance with the intended purposes. In this case, the content of a compound of formula (I) in the formulations will usually be satisfactory if it is the same as that of the effective component in conventional formulations:

namely, 0.5 to 95%, preferably 2 to 70%. As for the content of the adjuvants it is 99.5 to 5%, preferably 98 to 30%.

As carriers, both solid and liquid ones can be used. The solid carriers include clay, kaolin, talc, diatomaceous earth, silica, and calcium carbonate, and the liquid carriers include alcohols, acetone, xylene, toluene, methylnaphthalene, cyclohexane, dimethylformamide, dimethylsulfoxide, animal or vegetable oils, fatty acids, fatty acid esters, and many kinds of surface active agents.

Adjuvants other than carriers usually used for agricultural chemicals such as spreading agents, emulsifiers, wetting agents, dispersing agents and fixing agents can be properly mixed in order to assure the desired effects.

The compounds of the present invention can be used in the form of blends with other herbicides, insecticides, acaricides, agricultural and horticultural fungicides, soil fungicides, soil stabilizers or fertilizers.

Further detailed formulation examples of the present invention will be illustrated below. The kinds of adjuvants and the mixing ratios should not be limited within the range of the examples but can be utilized in wider ranges for practical uses.

In the following examples, parts are given by weight.

Formulation Example 1

Dust:

10 parts of Compound No. 1 of the present invention [N-(1-ethylthio-2,2,2-trichloroethyl)-2-acetoxybenzamide], 41 parts of talc and 49 parts of clay were mixed together and pulverized to obtain a dust.

Formulation Example 2

Wettable powders:

80 parts of Compound No. 18 of the present invention [N-(1-iso-propylthio-2,2,2-trichloroethyl)-2-hydroxybenzamide], 15 parts of kaolin, 3 parts of sodium higher alcohol sulfate and 2 parts of sodium polyacrylate were mixed together and pulverized to obtain a wettable powder.

Formulation Example 3

Granules:

3 parts of Compound No. 25 of the present invention [N-(1-phenylthio-2,2,2-trichloroethyl)-2-hydroxybenzamide], 35 parts of diatomaceous earth, 23 parts of bentonite, 37 parts of talc and 2 parts of a disintegrator were mixed together and 18 parts of water was added thereto to moisten the mixture homogeneously. Then, the mixture was extruded through an injection molding machine to obtain granules, which were then dried, treated in a crusher and regranulated by means of a granulator to obtain granules having a particle size of 0.6 to 1 mm.

Formulation Example 4

Micro granules:

5 parts of Compound No. 15 of the present invention [N-(1-methylthio-2,2,2-trichloroethyl)-2-hydroxybenzamide] was homogeneously mixed with 6 parts of bentonite and 9 parts of clay to make a concentrated powder mixture.

Separately, 80 parts of non-absorbent coarse mineral powder of 105 to 74 microns was placed in a proper mixing machine, into which 20 parts of water was added under rotation to moisten the powder and then the above-mentioned concentrated powder mixture was added thereto to coat the same. The products were dried to obtain micro granules.

Formulation Example 5

Emulsion:

20 parts of Compound No. 17 of the present invention [N-(1-n-propylthio-2,2,2-trichloroethyl)-2-hydroxybenzamide] was dissolved in 63 parts of xylene, into which 17 parts of a mixture of alkylphenol-ethylene oxide condensate and calcium alkylbenzenesulfonate (8:2) was mixed and dissolved to obtain an emulsion. The emulsion is to be used after dilution with water.

The advantageous effects of the present invention will be shown by the following experimental results.

Test Example 1

Test on prevention of Chinese cabbage clubroot:

A pot of 15 cm diameter was filled with soil infected by *Plasmodiophora brassicae* and mixed with a 10% dust of the compound of the present invention prepared by the same procedure as in Formulation Example 1 in an amount of 2 g in each pot. Thereafter, 15 seeds of Chinese cabbage (variety: Taibyo 60-nichi) were sowed in each pot.

The pot was transferred to field.

A dust containing 20% of PCNB (active ingredient: pentachloronitrobenzene) was used as a control and tested in the same procedure as mentioned above.

4 weeks after sowing, the Chinese cabbage were taken up and the degree of the attack by the fungus was observed.

Percentage of healthy seedlings was calculated as follows:

Percentage of healthy seedlings = $\frac{\text{Number of healthy seedlings in each pot}}{\text{Number of observed seedlings in each pot}} \times 100$ The results are shown in Table 2.

TABLE 2

| Compound No. | Active component quantity (per pot) | Percentage of healthy seedlings | Phytotoxicity |
|---|---|---|---|
| Compound of the present invention | | | |
| 1 | 0.02 g | 86% | nil |
| 2 | 0.02 g | 100 | nil |
| 3 | 0.02 g | 100 | nil |
| 4 | 0.02 g | 100 | nil |
| 5 | 0.02 g | 100 | nil |
| 6 | 0.02 g | 100 | nil |
| 7 | 0.02 g | 100 | nil |
| 8 | 0.02 g | 90 | nil |
| 9 | 0.02 g | 88% | nil |
| 10 | 0.02 g | 86 | nil |
| 11 | 0.02 g | 85 | nil |
| 12 | 0.02 g | 89 | nil |
| 13 | 0.02 g | 85 | nil |
| 14 | 0.02 g | 89 | nil |
| 15 | 0.02 g | 95 | nil |
| 16 | 0.02 g | 87 | nil |
| 17 | 0.02 g | 96 | nil |
| 18 | 0.02 g | 100 | nil |
| 19 | 0.02 g | 100 | nil |
| 20 | 0.02 g | 100 | nil |
| 21 | 0.02 g | 100 | nil |
| 22 | 0.02 g | 98 | nil |
| 23 | 0.02 g | 96 | nil |
| 24 | 0.02 g | 86 | nil |
| 25 | 0.02 g | 100 | nil |
| 26 | 0.02 g | 100 | nil |
| 27 | 0.02 g | 90 | nil |
| 28 | 0.02 g | 100 | nil |
| 29 | 0.02 g | 100 | nil |

TABLE 2-continued

| Compound No. | Active component quantity (per pot) | Percentage of healthy seedlings | Phyto-toxicity |
|---|---|---|---|
| 30 | 0.02 g | 100 | nil |
| 31 | 0.02 g | 93 | nil |
| 32 | 0.02 g | 90% | nil |
| 33 | 0.02 g | 95 | nil |
| 34 | 0.02 g | 92 | nil |
| control | | | |
| Dust containing 20% PCNB | 0.02 g | 85 | nil |
| untreated | — | 4 | — |

Test Example 2

Test on prevention of rice blast:

About 50 grains of rice (variety: Saitama mochi No. 10) was sowed in each pot (15 cm × 5 cm × 10 cm). After 20 days, seedlings (stage of 2 to 3 leaves) was applied with a prescribed quantity of 10% granules of the compound of the present invention prepared by the same procedure as in Formulation Example 3. Then the seedlings were infected by spraying with the solution in which spores of *Pyrcuralia oryzae* were suspended.

Then the seedlings were transferred into a greenhouse.

Granules containing 17% of IBP (active ingradient: 0,0-di-iso-propyl-S-benzylphosphorothioate) was used as a control and test in the same procedure as mentioned above.

20 days after inoculation, the degree of the attack by the fungus was observed. Control (Prevention) value was calculated as follows:

$$\text{Control value} = \frac{\text{Attack index of non-treated pot-attack index of treated pot}}{\text{Attack index of non-treated pot}} \times 100$$

$$\text{provided: attack index} = \frac{\text{Number of dead leaves by attack}}{\text{Total number of leaves}} \times 100$$

The results are shown in Table 3

TABLE 3

| Compound No. | Active component quantity (per pot) | Percentage of healthy seedlings | Phyto-toxicity |
|---|---|---|---|
| Compound of the present invention | | | |
| 3 | 20 mg | 76 | nil |
| 8 | 20 mg | 74 | nil |
| 15 | 20 mg | 84 | nil |
| 16 | 20 mg | 80 | nil |
| 18 | 20 mg | 92 | nil |
| Control | | | |
| Dust containing 17% IBP | 20 mg | 72 | nil |
| untreated | — | 12 | — |

Test Example 3

Test on prevention of damping off of cucumber:

A pot of 12 cm diameter was filled with field soil, which was infected by adding 5 g per pot of pathogenous soil cultivated by *Rhizoctonia solani*. Then 10 seeds of cucumber (variety: Ohyashima) were sowed in a pot and 80% wettable powders of the compound of the present invention prepared by the same procedure as in Formulation Example 2 were poured upon them in an amount of 50 ml in each pot after dilution with water.

Wettable powders containing 50% of PCNB (active ingredient: pentachloronitrobenzene) were used as a control and tested in the same procedure as mentioned above.

10 days after sowing, the degree of the attack by the fungus was observed.

Percentage of healthy seedlings was calculated as follows:

$$\text{Percentage of healthy seedlings} = \frac{\text{Number of healthy seedlings in each pot}}{\text{Number of emerged seedlings in untreated and uninfected pot}} \times 100$$

The results are shown in Table 4.

TABLE 4

| Compound No. | Active component quantity (per pot) | Percentage of healthy seedlings | Phyto-toxicity |
|---|---|---|---|
| Compound of the present invention | | | |
| 1 | one thousand ppm | 82 | nil |
| 3 | one thousand ppm | 85 | nil |
| 4 | one thousand ppm | 78 | nil |
| 15 | one thousand ppm | 88 | nil |
| 19 | one thousand ppm | 76 | nil |
| Control | | | |
| Dust containing 20% PCNB | one thousand ppm | 80 | nil |
| untreated | — | 0 | — |

What we claim is:

1. A compound represented by the formula:

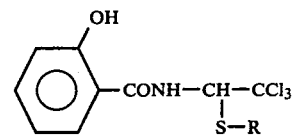

wherein R is alkyl having 1–12 carbon atoms.

2. The compound according to claim 1, wherein R is alkyl having 1–4 carbon atoms.

3. The compound according to claim 2, wherein R is CH₃.

4. The compound according to claim 2, wherein R is C₂H₅.

5. The compound according to claim 2, wherein R is C₃H₇(iso).

6. A fungicidal composition for agriculture and horticulture comprising 0.5 to 95% by weight of a compound of the formula:

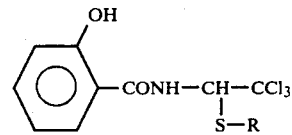

wherein
R is alkyl having 1–12 carbon atoms, and 99.5 to 5% by weight of inert adjuvants.
7. A method for preventing diseases of agricultural or horticultural plants caused by fungi comprising applying to said plants a fungicidally effective amount of a compound represented by the formula:
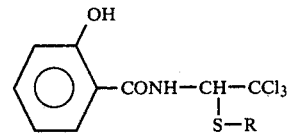
wherein R is alkyl having 1–12 carbon atoms.
* * * * *